United States Patent
Cha

(10) Patent No.: US 6,400,983 B1
(45) Date of Patent: Jun. 4, 2002

(54) APPARATUS FOR ANALYZING BODY COMPOSITION USING NOVEL HAND ELECTRODES AND METHOD THEREOF

(75) Inventor: Ki Chul Cha, Seoul (KR)

(73) Assignee: Biospace Co. Ltd. (KR)

( * ) Notice: Subject to any disclaimer, the term of this patent is extended or adjusted under 35 U.S.C. 154(b) by 0 days.

(21) Appl. No.: 09/495,097

(22) Filed: Feb. 1, 2000

(30) Foreign Application Priority Data

Aug. 9, 1999 (KR) .............................. 99-32644

(51) Int. Cl.[7] .................................................. A61B 5/05
(52) U.S. Cl. ...................................................... 600/547
(58) Field of Search ................................ 600/300, 345, 600/384, 386, 393, 547

(56) References Cited

U.S. PATENT DOCUMENTS

| | | | |
|---|---|---|---|
| 4,895,163 A | 1/1990 | Libke et al. ................ 128/734 |
| 4,911,175 A | 3/1990 | Shizgal ....................... 128/734 |
| 5,335,667 A | 8/1994 | Cha et al. ................... 128/734 |
| 5,372,141 A | * 12/1994 | Gallup et al. ............... 128/734 |
| 5,720,296 A | 2/1998 | Cha ............................ 128/734 |
| 5,817,031 A | * 10/1998 | Masuo et al. ............... 600/547 |
| 6,208,890 B1 | * 3/2001 | Sarrazin et al. ............ 600/547 |

* cited by examiner

*Primary Examiner*—Marvin M. Lateef
*Assistant Examiner*—Jeoyuh Lin
(74) *Attorney, Agent, or Firm*—Woodcock Washburn LLP

(57) ABSTRACT

The present invention relates to an apparatus and a method for analyzing body composition using a hand electrode apparatus for improving the precision in measuring the upper body impedance by passing a weak, alternating current across the body through the current electrodes and reading the voltage difference. The voltage electrodes are located outside the current pathway to give a more accurate measurement of body impedance.

6 Claims, 8 Drawing Sheets

APPARATUS FOR ANALYZING BODY COMPOSITION USING NOVEL HAND ELECTRODES AND METHOD THEREOF

FIELD OF THE INVENTION

The present invention relates to an apparatus and a method for analyzing body composition based on bioelectrical impedance analysis (BIA). More particularly, the present invention relates to an apparatus and a method for analyzing body composition using a hand electrode apparatus for improving the precision in measuring the upper body impedance by passing a weak, alternating current across the body through the current electrodes and reading the voltage difference.

BACKGROUND OF THE INVENTION

A human body is composed of water, protein, bone, and fat, in addition to a small amount of special components. The total of these elements constitutes the body weight. Quantitatively measuring the respective elements is called body composition analysis. Recent years body composition analyzers have been actively developed due to interest in health care from fatness. The proportion occupied by the fat is called fatness and is used in diagnosing various adult diseases. Especially, the water portion is the main component for supporting the human body and the amount thereof is related to the amount of muscle generating energies. Thus, the amount of muscle in body is applied widely as an index indicating nutritive conditions. In the medical terms, patients suffering from malnutrition related, for example, to cancer are subjected to a periodically measuring the amount of muscle in body to determine remission state or to monitor progress of the disease. Further, the growth in child body and the nutrition status of elderly men can be diagnosed on basis of the analysis of the amount of muscle. Accordingly, an analysis of the body composition has been used as basic means to examine a person and needs for the precision in measuring the body composition have been increased. As one of conventional methods for measuring the body composition, bioelectrical impedance analysis (BIA) is widely employed. This method has advantages such as safety, fastness, and low cost in comparison with the other conventional methods. This method is carried out the following manner. That is, a weak alternating current is passed across the human body to analyze the body composition by measuring the electrical resistance or the impedance of the body.

A basic principle to measure the body composition by using BIA, is as follows: where rich in water, a weak alternating current flows easily so that a low resistance value is obtained. While, where insufficient in water the current is difficult to flow so that a high resistance value is obtained. As muscle contains the most water in the body, each amount of muscle and body fat may be measured on the above-mentioned principle. The apparatus for analyzing the human composition substitutes body height, weight, age, gender, and measured impedance of the human subject into the specific expression to calculate the body composition, and displays the analyzed results on the LCD display unit.

FIG. 1 shows the conventional embodiment of determining the upper body composition by measuring the impedance between both hands. As shown In FIG. 1(a), a person in an upright posture grasps a pair of electrodes comprising a left electrode and a right electrode, with arms stretched to the front. In the embodiment, upper palm electrodes 5, 7 contact with the upper part of a palm and fingers, and lower palm electrodes 6, 8 contact with the lower part of a palm and fingers, and the human subject locates the center of hands on the boundary between the upper hand electrode and the lower hand electrode to contact with the current electrode and the voltage electrode. As shown in FIG. 1(c), the electrodes contact with the palm and the fingers to be connected electrically with the body. However, the method has the disadvantage that the variation in the contact location between the electrode and the body depends on the grip posture and the change of contact area between the electrode and the body depends on the grip intensity, resulting in a low reproducibility of the measurement.

FIG. 2 represents another embodiment of determining the upper body composition by measuring the impedance between the right and left hand. The human subject grasps a column-shaped current electrode on the right and left side of the apparatus and contacts the right and left wrist on a voltage measuring electrode. The apparatus passes the electric current across the body through the column-shaped electrode and reads voltage differences between wrist electrodes used as the voltage electrodes. However, some variations in the contact location and the contact region are inevitable even for the same person, which results in a low reproducibility of the measurement. Further, the individual difference in the body size, for example the difference in arm length between an adult and a child, raises the deviation of the contact location.

In the prior arts, the accuracy and reproducibility of measurement highly count on how to grip the electrodes when the measurement is carried out for the untrained person. Thus, variations in contact location and contact region are inevitable and affect the measured value.

The present inventor developed an apparatus for analyzing body composition based on bioelectrical impedance analysis, which is disclosed in U.S. Pat. No, 5,720,296 and Korean patent No. 123,408 and No. 161,602. The inventions improve the accuracy in analyzing the body composition and can measure segmental impedances by using an electronic switch which is controlled by a micro-processor. However, the apparatus has disadvantages in portability.

Thus, in the method measuring the impedance between two arms by measuring the voltage difference between the voltage electrodes, the present inventor has invented an apparatus for analyzing body composition, which can improve the precision by minimizing factors to affect measurement results, when measurement is carried out repeatedly for individuals or the same person without a specially trained examiner.

OBJECTS OF THE INVENTION

An object of the present invention is to provide an apparatus for analyzing upper body composition, in which the upper body composition can be analyzed conveniently by passing an electric current across the body through the current electrodes and measuring the impedance between voltage electrodes.

Another object of the present invention is to provide an apparatus for measuring the upper body composition in which if palm electrodes are used as a current electrode, then thumb electrodes are used as a voltage electrode, and if thumb electrodes are used as a current electrode, then palm electrodes are used as a voltage electrode, so as to improve accuracy and reproducibility in the measurement.

A further object of the present invention is to provide a simple and portable apparatus for measuring the body composition which uses only hand electrodes to measure the upper body impedance.

A further object of the present invention is to apply the electrode method, in which a measuring person grips column electrode and contacts his thumbs to thumb electrodes, to other apparatuses measuring the upper body impedances.

The above objects and other advantages of the present invention will be apparent from the ensuing disclosure and appended claims.

SUMMARY OF THE INVENTION

A handle-shaped apparatus for analyzing the body composition based on the bioelectrical impedance analysis according to the present invention comprises: a right palm electrode 1 and a left palm electrode 3 located on the right and left side of said apparatus, contacting with each inner surface of the right and left palm and fingers excluding a thumb; a right thumb electrode 2 and a left thumb electrode 4 located by the side of said palm electrodes, so that a measuring person can grasp said palm electrodes and contact said thumb electrodes with the right and left thumbs; an impedance measuring circuit 15 for measuring the impedance based on a voltage-current ratio by making an alternating current flow between two of the electrodes with a current generator 13 therein and reading the voltage difference with a voltage meter 14 therein; an amplifier 16 and A/D converter 17 for interfacing the impedance measuring circuit 15, to a microprocessor; a keyboard 18 to input the body height, weight, gender, and age; the microprocessor 19 processing the data received from the impedance measuring circuit 15 and the keyboard 18; and a display unit 20 for to display the results processed by the microprocessor 19, thereby the apparatus locates voltage electrodes outside of the current pathway to measure the upper body impedances, highly reproducibly irrespective of the grip posture and grip intensity. In the body composition analyzing apparatus of the present invention, the results processed by the microprocessor are shown on the display.

The apparatus of this invention may be equipped with an interface for connecting an outside computer.

BRIEF DESCRIPTION OF THE DRAWINGS

FIG. 1(*b*) is a plane figure of the conventional apparatus for measuring the upper body impedances;

FIG. 1(*c*) illustrates hand regions contacting with the conventional apparatus for measuring the upper body impedances;

FIG. 2(*b*) is a plane figure of another conventional apparatus for measuring the upper body impedances;

FIG. 2(*c*) illustrates hand regions contacting with another conventional apparatus for measuring the upper body impedances;

FIG. 3(*b*) is a plane figure of the apparatus for measuring the upper body impedances according to the present invention;

FIG. 3(*c*) illustrates hand regions contacting with the apparatus for measuring the upper body impedances according to the present invention;

DETAILED DESCRIPTION OF THE PREFERRED EMBODIMENT

Reference will now be made to the drawings wherein like structures will be provided with like reference designations.

Figure 1A:
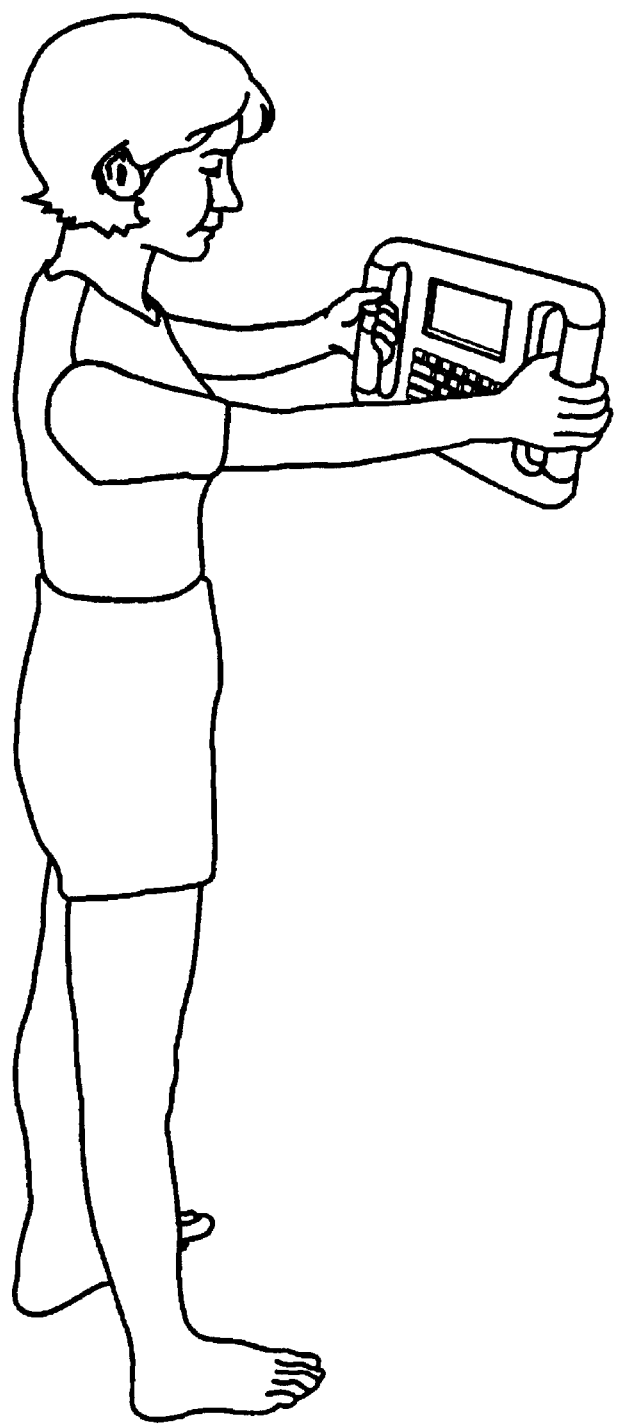
FIG. 1(*a*) is a schematic view showing the conventional embodiment for measuring the upper body impedances.
Figure 1B:
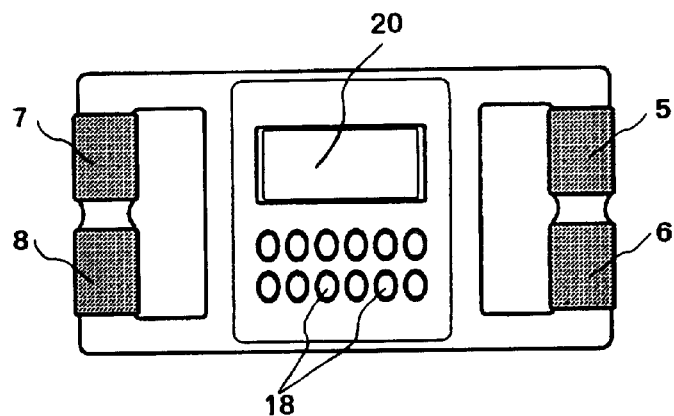
Figure 1C:
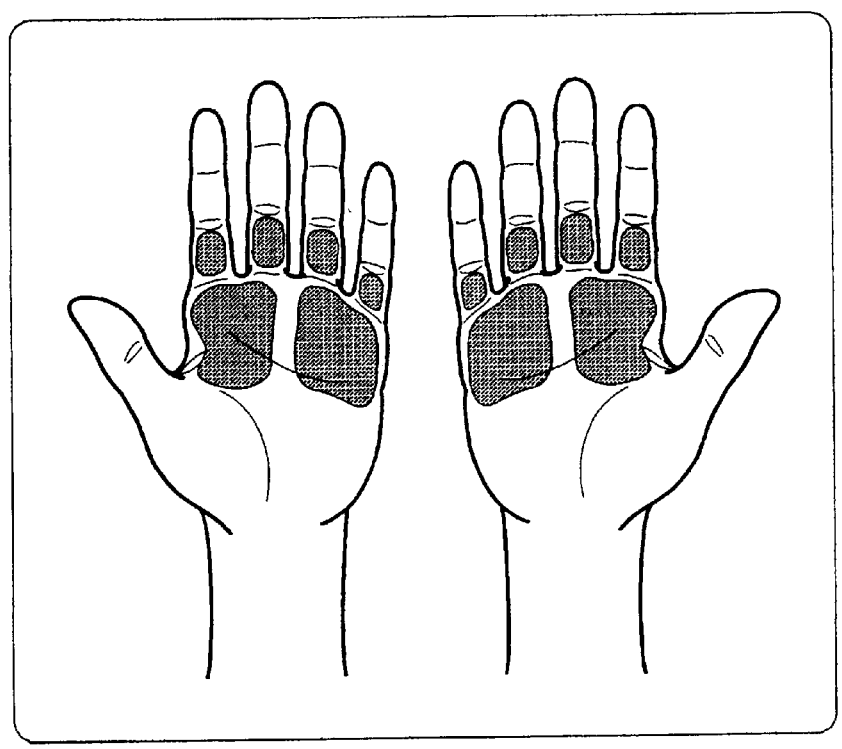
Figure 2A:
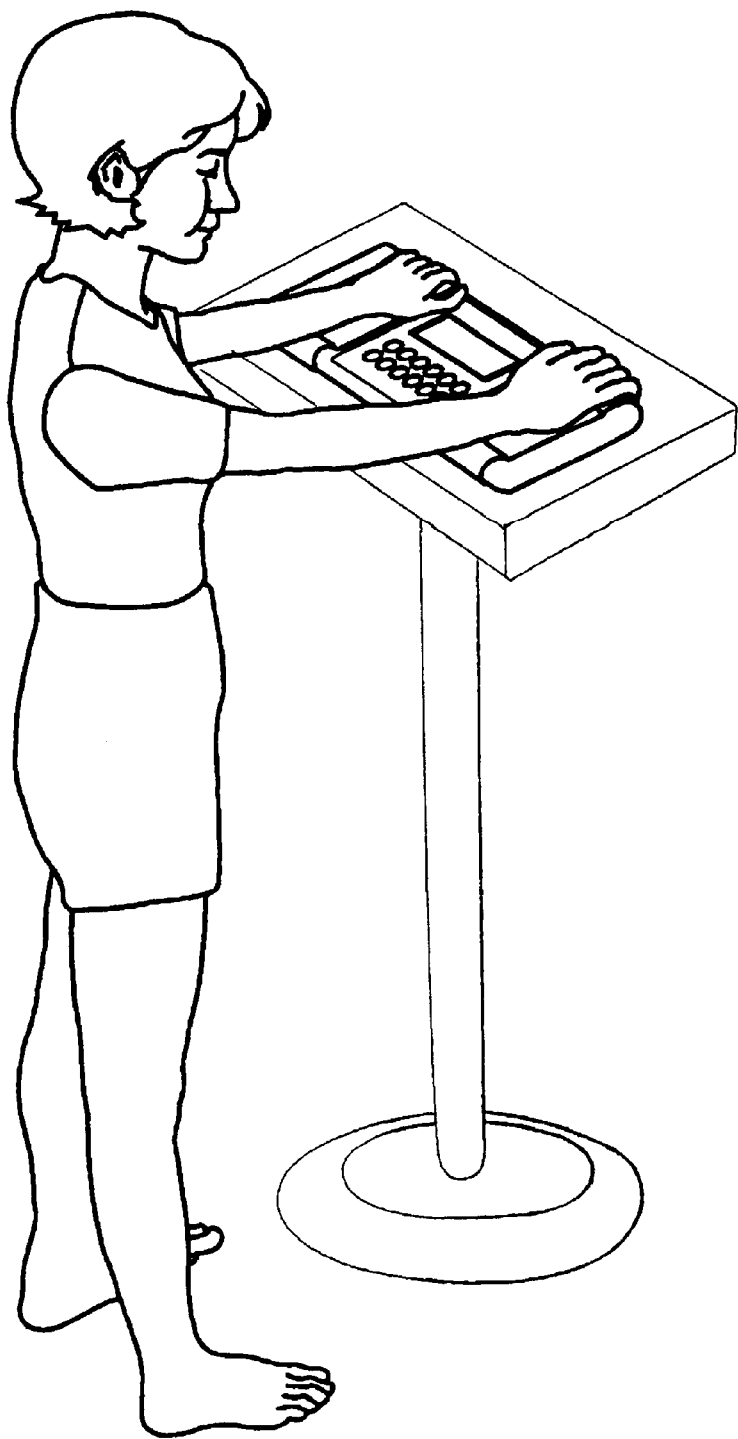
FIG. 2(*a*) is a schematic view showing an embodiment for measuring the upper body impedances using another conventional measuring method.
Figure 2B:
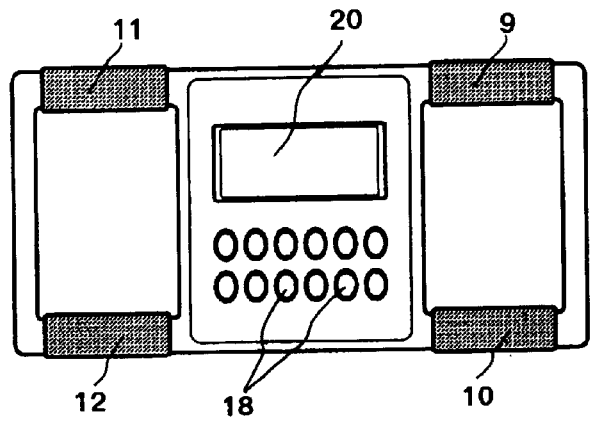
Figure 2C:
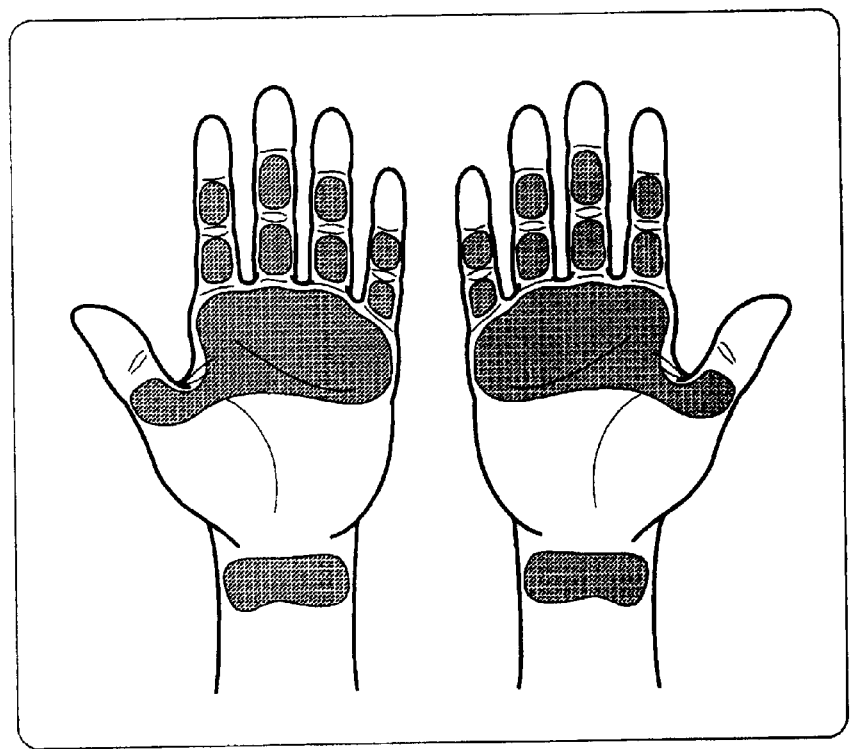
Figure 3A:
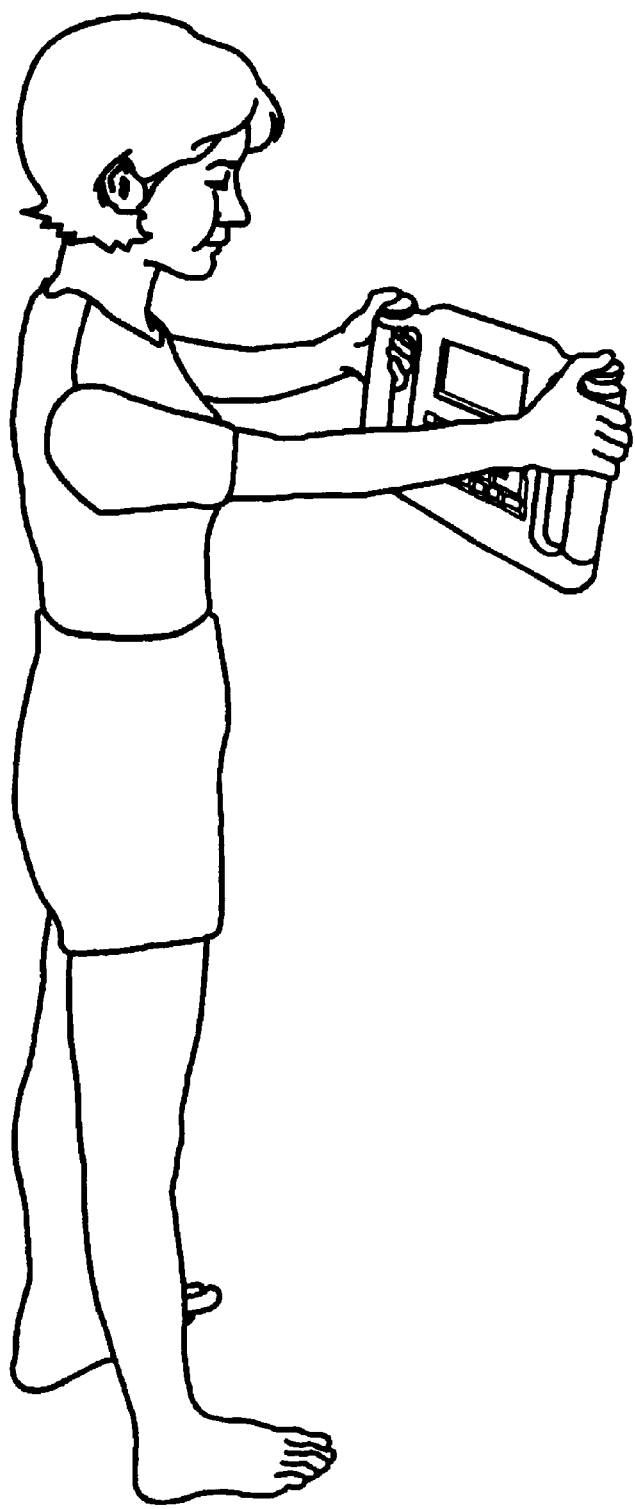
FIG. 3(*a*) is a schematic view showing an embodiment for measuring the upper body impedances using the hand electrode method according to the present invention.
Figure 3B:
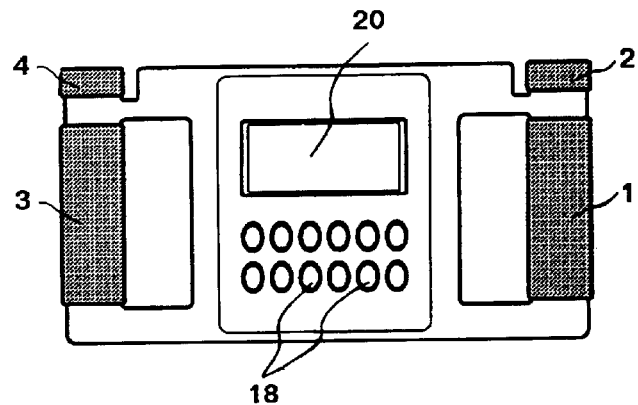
Figure 3C:
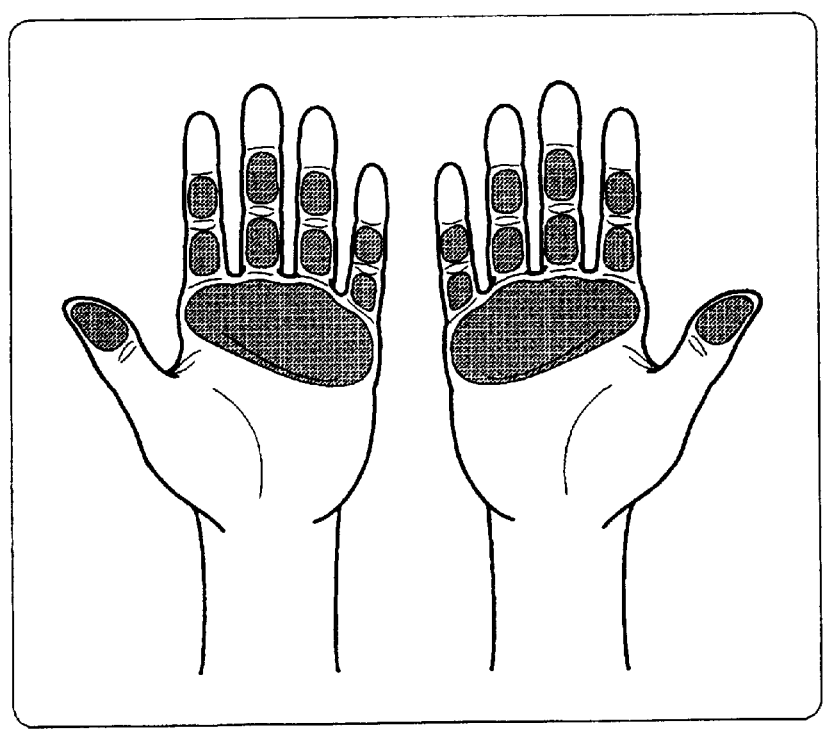

FIG. 3 is a schematic view showing an embodiment for measuring the upper body impedances using the hand electrode method according to the present invention.

A body composition analyzer of this invention comprises: a right palm electrode 1 located on the right side of the apparatus, contacting with inner surfaces of the right palm and fingers excluding a thumb; a right thumb electrode 2 for contacting with only a right thumb; a left palm electrode 3 located on the left side of the apparatus, contacting with inner surfaces of the left palm and fingers excluding a thumb; and a left thumb electrode 4 for contacting with only a left thumb. Thus, the body composition analyzing apparatus according to the present invention is in a handle shape, wherein the right and left sides are used as palm electrodes and the thumb electrodes are located by the side of the palm electrodes, so that a human subject may grip palm electrodes and press the thumbs on the thumb electrodes. A measuring person stretches arms to the front in a standing posture and an electric current flows into the body through the palm electrodes used as current electrodes so that the impedance is measured by reading the voltage difference between the thumb electrodes used as voltage electrodes.

Each of the electrodes 1–4 serves as a current electrode or a voltage electrode. If the electrodes 1, 3 are used as current electrodes, then the electrodes 2, 4 are used as voltage electrodes. On the other hand, if the electrodes 2, 4 are used as current electrodes, then the electrodes 1, 3 are used as voltage electrodes, which can be conducted by a person with ordinary skills in the art.

Figure 4:
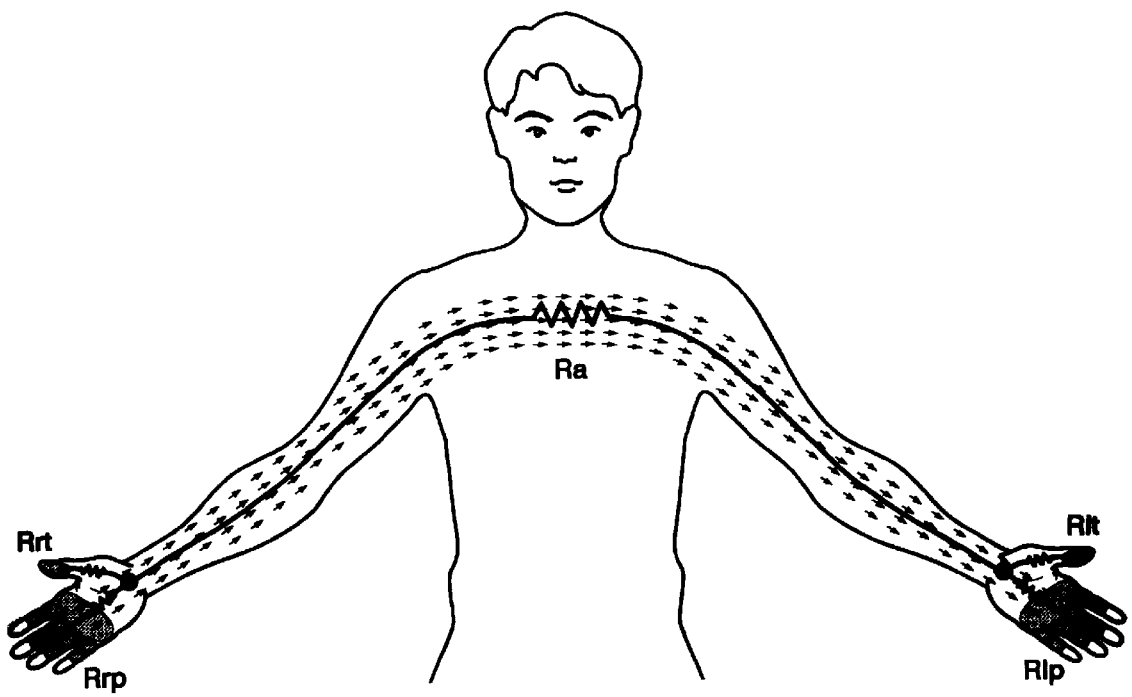
FIG. 4 schematically illustrates an impedance model of a human body to be measured by the apparatus according to the present invention.

FIG. 4 schematically illustrates an impedance model of a human body to be measured by the apparatus according to the present invention.

It will be indicated as follows:

The resistance from the right wrist to the left wrist is indicated by $R_a$, the resistance from the right wrist to the right thumb is indicated by $R_{rt}$, the resistance from the left wrist to the left thumb is indicated by $R_{lt}$, the resistance from the right wrist to the right palm is indicated by $R_{rp}$, and the resistance from the left wrist to the left palm is indicated by $R_{lp}$.

Figure 5:
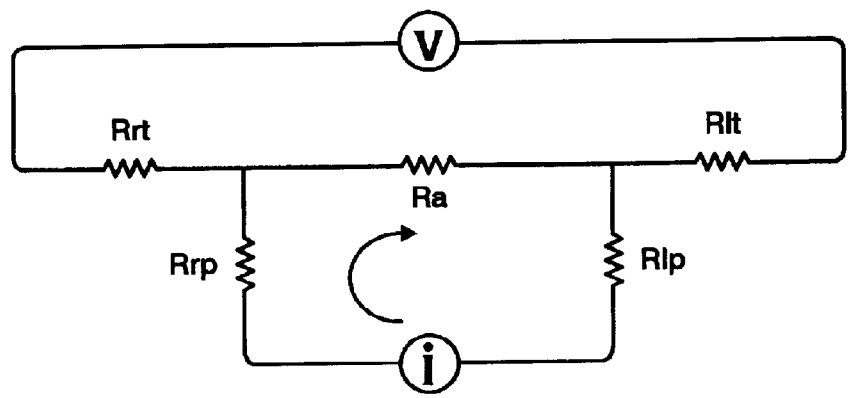
FIG. 5 is an electric circuit illustrating schematically the principle measuring the upper body impedances according to the present invention.

FIG. 5 is an electric circuit illustrating schematically the principle measuring the upper body impedances according to the present invention.

The electric current flows in order of $R_{rp}$, $R_a$, and $R_{lp}$ in the body through two palm electrodes. The measured voltage difference between the thumb electrodes means the voltage difference between both ends of $R_a$, the impedance values of the portion where the electric current flows. At this moment, the measured values are not affected by $R_{rp}$, $R_{lp}$, $R_{rt}$, and $R_{lt}$.

The above-mentioned principle has important meanings in view of the technique. When a person grips the electrodes, the variation of contact location between the body and the electrodes depends significantly on the grip. In the conventional method, said variations in contact location have a direct effect on the measured results. Therefore, the determined values are changeable for each test. On the contrary, according to this invention the variations of $R_{rt}$, $R_{lt}$, $R_{rp}$, and $R_{lp}$ have no influence on $R_a$, which is the upper body resistance. Therefore, this method is highly evaluated as it can improve the measurement precision.

Figure 6:
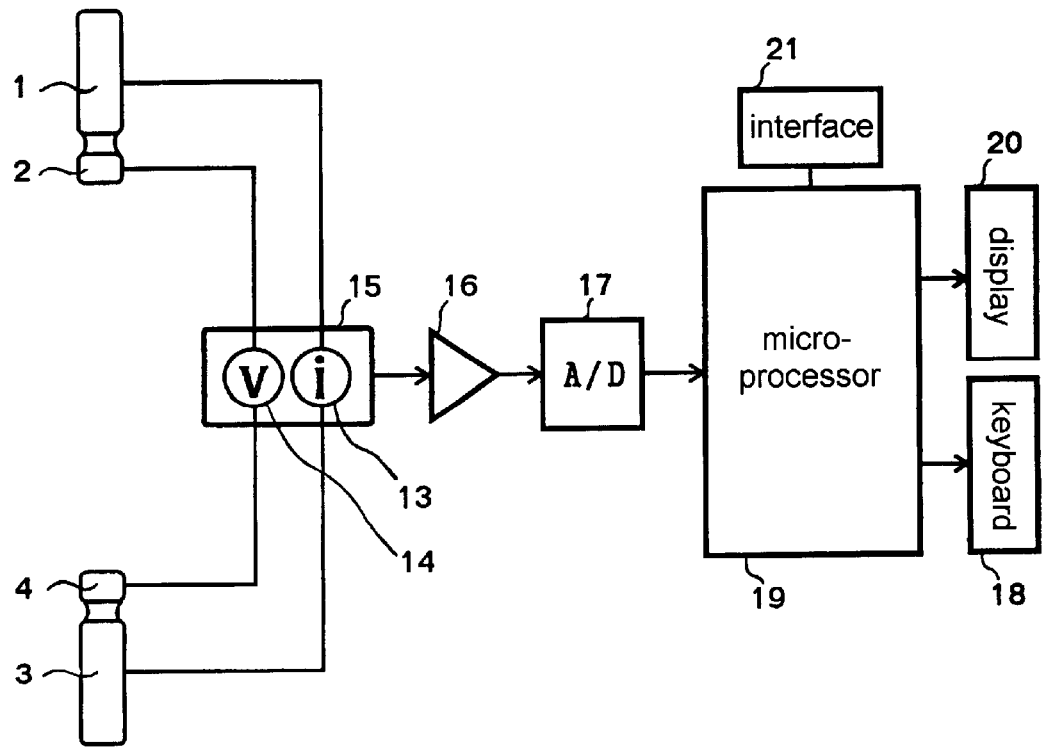
FIG. 6 illustrates the circuit of the body composition analyzing apparatus according to the present invention.

FIG. 6 illustrates the circuit of the body composition analyzing apparatus according to the present invention.

The current generator 13 in the impedance measuring circuit 15 for measuring the impedance makes an alternating current flow at the frequency of between 1 kHz and 1000 kHz and flows the current into the body, and the voltage meter 14 reads the voltage difference between two voltage electrodes. The signals measured by the impedance measuring circuit 15 are transferred to the microprocessor 19 through the amplifier 16 and the A/D converter 17. The weight, body height, age and gender of the measuring person are inputted through a keyboard and are processed along with the data received from the impedance measuring circuit by the microprocessor 19, which controls the storage, calculation, and output of the data. The results of the analysis can be shown on the display unit 20.

The apparatus of this invention may be equipped with an interface 21 for connecting outside computers for further calculation and storage of the data.

Examples for computing the body composition from the measured impedances, body height, weight and gender are as follows.

The amount of water contained in the body is proportional to $Ht^2/R$, wherein R is the impedance or the resistance and Ht is the height of the measuring person.

The total body water (TBW) in the body is defined as follows:

$$TBW = C_1 Ht^2/R_a + C_2 Wt + C_3 GENDER + C_4 AGE + C_5 \quad (I)$$

wherein $C_1$, $C_2$, $C_3$, $C_4$, and $C_5$ are the best suitable constants, Ht, Wt, GENDER, AGE are respectively, the height, weight, gender, and age of the measuring person.

Equation (I) is stored in the microprocessor, and therefore, TBW can be obtained from the measured impedances and the input data.

Body fat contains relatively small amount of water, and therefore, this water content is disregarded. The fat free mass (FFM) contains about 73% of water, therefore FFM is defined as follows:

$$FFM = TBW/0.73 \quad (II)$$

The amount of body fat (FAT) is defined to be the weight (Wt) minus FFM, and is defined by Equation (III), thus percent body fat (% BF) is defined by Equation (IV) as follows:

$$FAT = Wt - FFM \quad (III)$$

$$\% BF = (Wt - FFM) \times 100/Wt \quad (IV)$$

The following example is given to illustrate the present invention and not intended as limitation thereof. Values in the table are in $\Omega$ unless otherwise specified.

EXAMPLE

This Example is carried out for five human subjects by means of the method as shown in FIG. 3. The resistances were measured repeatedly five times per each subject with the grip varied per each test. An alternating current in the magnitude of 800 mA at the frequency of 50 kHz flows into the body and the resistances were measured with BIA-101A model of RJL system Co. The test results are as set forth in Table 1, below:

TABLE 1

| Run | Subjects | | | | |
|---|---|---|---|---|---|
| | 1 | 2 | 3 | 4 | 5 |
| 1 | 633.0 | 653.0 | 1016.0 | 767.0 | 581.0 |
| 2 | 628.0 | 648.0 | 1020.0 | 754.0 | 578.0 |
| 3 | 638.0 | 663.0 | 1024.0 | 761.0 | 587.0 |
| 4 | 629.0 | 651.0 | 1020.0 | 755.0 | 586.0 |
| 5 | 624.0 | 655.0 | 1018.0 | 756.0 | 584.0 |
| Average | 629.4 | 654.0 | 1019.6 | 758.6 | 583.2 |
| The standard deviation | 3.8 | 5.7 | 3.0 | 5.4 | 3.7 |

The above results show that though different resistances are obtained for each of the subjects, the reproducible results for one person are obtained irrespective of the grip posture.

COMPARATIVE EXAMPLES

Comparative Examples 1~2 were carried out in the same manner as the Example except that the conventional electrode method were applied. The test results are presented in Table 2~3.

TABLE 2

| Run | Subjects | | | | |
|---|---|---|---|---|---|
| | 1 | 2 | 3 | 4 | 5 |
| 1 | 681.0 | 689.0 | 1086.0 | 807.0 | 628.0 |
| 2 | 662.0 | 642.0 | 1120.0 | 824.0 | 660.0 |
| 3 | 679.0 | 679.0 | 993.0 | 782.0 | 618.0 |
| 4 | 657.0 | 660.0 | 986.0 | 756.0 | 637.0 |
| 5 | 651.0 | 699.0 | 1060.0 | 821.0 | 610.0 |
| Average | 660.0 | 673.8 | 1049.0 | 798.0 | 630.6 |
| The standard deviation | 13.4 | 22.9 | 58.4 | 28.7 | 19.3 |

TABLE 3

| Run | Subjects | | | | |
|---|---|---|---|---|---|
| | 1 | 2 | 3 | 4 | 5 |
| 1 | 429.0 | 443.0 | 731.0 | 489.0 | 416.0 |
| 2 | 489.0 | 426.0 | 770.0 | 555.0 | 492.0 |
| 3 | 468.0 | 463.0 | 677.0 | 459.0 | 500.0 |
| 4 | 415.0 | 477.0 | 842.0 | 413.0 | 414.0 |
| 5 | 449.0 | 418.0 | 817.0 | 529.0 | 446.0 |
| Average | 450.0 | 445.4 | 767.4 | 489.0 | 453.6 |
| The standard deviation | 29.6 | 24.7 | 66.2 | 56.2 | 40.8 |

When the test is carried out with the grip varied, the test results according to the conventional methods show the large standard deviations. That is to say, the grip posture and the grip intensity cause the contact location to vary inevitably, which has significant effects on the test results. While the test results measured according to this invention show the small standard deviations. As a result of analyzing the anatomical structure and of contemplating the contact location between the electrode and the body, the apparatus according to this invention locates voltage electrodes outside of the current pathway to measure the upper body impedances highly reproducibly irrespective of the grip posture and grip intensity.

It should be apparent to those skilled in the art that various changes and modifications can be added to the present invention without departing from the scope of the present invention, which is limited only by the appended claims.

What is claimed is:

1. An apparatus for analyzing body composition based on bioelectrical impedance analysis, which comprises:

a right palm electrode and a left palm electrode located on the right and left side of the apparatus;

a right thumb electrode and a left thumb electrode located by the sides of each of the palm electrodes, wherein either the right and left thumb electrodes are voltage electrodes and the right and left palm electrodes are current electrodes or the right and left thumb electrodes are current electrodes and the right and left palm electrodes are voltage electrodes;

an impedance measuring circuit for measuring impedance based on a voltage-current ratio by making an alternating current flow between two of the electrodes with a current generator therein and reading voltage difference with a voltage meter therein;

an amplifier and A/D converter for interacting the impedance measuring circuit to a microprocessor;

means for inputting data related to the body;

a microprocessor processing the data received from the impedance measuring circuit and a keyboard; and a display unit for displaying the results processed by the microprocessor, wherein the voltage electrodes are located outside of the current pathway.

2. The apparatus as claimed in claim 1, wherein said palm electrodes are used as current electrodes and said thumb electrodes are used as voltage electrodes.

3. The apparatus as claimed in claim 1, a current between 1 kHz and 1000 kHz in the various frequency range is generated by the current generator.

4. The apparatus as claimed in claim 1, further comprising an interface for connecting outside computers for further calculation and storage of the data.

5. The apparatus as claimed in claim 1, wherein said palm electrodes are used as voltage electrodes and thumb electrodes are used as current electrodes.

6. A method for measuring the body composition of a user based on bioelectrical impedence, comprising the steps of:

(a) providing an apparatus for analyzing body composition based on bioelectrical a impedence analysis, which comprises:

a right palm electrode and a left palm electrode located on the right and left side of the apparatus;

a right thumb electrode and a left thumb electrode located by the sides of each of the palm electrodes, wherein either the right and left thumb electrodes are voltage electrodes and the right and left palm electrodes are current electrodes or the right and left thumb electrodes are current electrodes and the right and left palm electrodes are voltage electrodes;

an impedance measuring circuit for measuring impedance based on a voltage-current ratio by making an alternating current flow between two of the electrodes with a current generator therein and reading voltage difference with a voltage meter therein;

an amplifier and A/D converter for interacting the impedance measuring circuit to a microprocessor;

means for inputting data related to the body;

a microprocessor processing the data received from the impedence measuring circuit and a keyboard; and a display unit for displaying the results processed by the microprocessor, wherein the voltage electrodes are located outside of the current pathway;

(b) grasping the apparatus such that the right and left palm electrodes are in contact with the right and left palms of the user, respectively, and the right and left thumb electrodes are in contact with the right and left thumbs of the user, respectively;

(c) measuring the body impedance of the user by passing a weak, alternating current across the body through the current electrodes and reading the voltage difference;

(d) amplifying the body impedance and converting the amplified impedance into digital signal thereof;

(e) inputting data related to the body; and (f) analyzing the body composition based on the measured impedance and inputting data; thereby voltage electrodes lie outside of the current pathway in the anatomical structure, which permit highly reproducible measurements to be accomplished irrespective of the grip posture and grip intensity.

\* \* \* \* \*